United States Patent
Soyama et al.

US007547339B2

(10) Patent No.: US 7,547,339 B2
(45) Date of Patent: Jun. 16, 2009

(54) FILTER MATERIAL TAKE-UP PRODUCT FOR AIR FILTER

(75) Inventors: Toshihiko Soyama, Nagaoka (JP); Masashi Sato, Nagaoka (JP)

(73) Assignee: Hokuetsu Paper Mills, Ltd., Niigata (JP)

( * ) Notice: Subject to any disclaimer, the term of this patent is extended or adjusted under 35 U.S.C. 154(b) by 1342 days.

(21) Appl. No.: 10/415,910

(22) PCT Filed: Sep. 26, 2001

(86) PCT No.: PCT/JP01/08365

§ 371 (c)(1), (2), (4) Date: May 5, 2003

(87) PCT Pub. No.: WO02/49935

PCT Pub. Date: Jun. 27, 2002

(65) Prior Publication Data

US 2004/0025479 A1    Feb. 12, 2004

(30) Foreign Application Priority Data

Dec. 21, 2000   (JP) ............................. 2000-388857

(51) Int. Cl.
*B01D 9/00*   (2006.01)
*B01D 39/14*   (2006.01)
*B65H 75/14*   (2006.01)

(52) U.S. Cl. .................. 55/356; 55/524; 242/610.1; 242/610.2

(58) Field of Classification Search ............ 55/524, 55/242; 243/610.1, 610.2; 242/610.1, 610.2
See application file for complete search history.

(56) References Cited

U.S. PATENT DOCUMENTS

| | | | | |
|---|---|---|---|---|
| 2,271,108 A | * | 1/1942 | Wade | .................... 313/580 |
| 5,593,482 A | * | 1/1997 | Dauber et al. | ............... 96/117.5 |
| 5,620,095 A | * | 4/1997 | Delmore et al. | ............. 206/438 |
| 5,845,871 A | * | 12/1998 | Lynch et al. | ............. 242/610.1 |
| 6,352,578 B1 | * | 3/2002 | Sakata et al. | .................. 96/134 |
| 6,506,184 B1 | * | 1/2003 | Villefrance | ................. 604/333 |

FOREIGN PATENT DOCUMENTS

| | | |
|---|---|---|
| JP | 07-052976 | 2/1995 |
| JP | 3021861 | 12/1995 |
| JP | 09-187612 | 9/1997 |
| JP | 10-244112 | 9/1998 |
| JP | 11-253715 | 9/1999 |

OTHER PUBLICATIONS

English Translation, Tadao Kobayashi, et al. Assembling, Packing and Performance Test Method of Air Filter, Assembling and Packing Method of Fan Filter Unit, CLean Room, and Local Equipment, Sep. 21, 1999.*
English Translation, Kenshi Isobashi, Winding-In Fixture for Winding Bulky Nonwoven Fabric, Dec. 13, 1995.*
International Preliminary Examination Report.

* cited by examiner

*Primary Examiner*—Walter D Griffin
*Assistant Examiner*—Amber Orlando
(74) *Attorney, Agent, or Firm*—James V. Costigan; Hedman & Costigan, P.C.

(57) ABSTRACT

A filter material take-up product and a paper winding core, which are free from secondary-contamination by an outgas while being transported or stocked. Irrespective of its application such as building air conditioner, an air cleaner or a semi-conductor factory, the amount of the outgas to be generated from the filter take-up product for the air filter can be kept at a negligible level. The filter take-up product for the air filter is produced by coating and wrapping the filter material for the air filter, as wound on the winding core, with a film wrapping material which is so made of phenolic compounds, carboxylate esters, phosphate ester or cyclic siloxance as to have an outgas generation in an amount of 100 ng/g or less by the dynamic head space method.

3 Claims, No Drawings

FILTER MATERIAL TAKE-UP PRODUCT FOR AIR FILTER

BACKGROUND OF THE INVENTION

1. Field of the Invention

The present invention relates to a filter material take-up product for an air filter. More particularly, the invention relates to a filter material take-up product for an air filter, which is used for a clean room, a clean bench or the like for a semiconductor, a liquid crystal or a bio/food industry, or an air filter for a building air conditioner, an air cleaner etc.

2. Description of the Related Art

A filter material for a high-efficiency particulate air (HEPA) filter, a filter material for an ultra low penetration air (ULPA) filter, and a filter material for an ASHRAE air filter, which are mainly made of a glass fiber, are used in various fields such as a clean room or a clean bench for a semiconductor, a liquid crystal or a bio/food industry, or an air filter for a building air conditioner, an air cleaner etc.

In connection with an increasing integration degree of LSI, there has been a major issue in a semiconductor manufacturing process in recent years: The issue is that a very small amount of a gas component (hereinafter referred to as an outgas) of a $ng/m^3$ order generated from the air filter and other components which constitute a clean room is stuck to a silicon wafer or a glass substrate, causing a reduction in yield of semiconductor products.

The outgas components which are considered problematic here mean organic substances in general that stick to the silicon wafer easily, and it is said that a polar substance sticks to the silicon wafer particularly easily.

Aside from the above, a recent environmental hormone problem, and a health hazard problem such as an allergy due to a volatile organic matter, represented by a sick building syndrome, have come under close scrutiny. Thus, there has been a need to heed the outgas from the air filter used for a building air conditioner or an air cleaner. Among carboxylate esters, di-2-ethylhexyl phthalate (DOP) and di-n-butyl phthalate (DBP) that are a phthalate ester, are particularly known as environmental hormones, and are substances to be controlled. As for a filter material for an air filter that solves this problem, a proposal has been made to limit a raw material used for a filter material in WO 97/04851, and Japanese Patent Laid-Open Heisei 10 (1998)-244112 etc.

On the other hand, the filter material for the air filter is continuously processed when pleating is carried out in a filter-processing maker. Thus, when shipped from a manufacturing factory of the filter material for the air filter, the filter is wound on a winding core made of paper, a synthetic resin, a metal or the like to be made in a shape of a take-up roll product. A packing method employed is wrapping the take-up roll by a film for the purpose of preventing it from being wet due to water, i.e., moisture prevention, as well as prevention of dusts and chips, while being transported or stored, and housing it in an outer box made of a cardboard or the like.

Regarding a packing method of an air filter unit, Japanese Patent Laid-Open Heisei 11 (1999)-253715 discloses a packing method by which an air filter is packed in a space where no gaseous organic matters exist, using a packing material which generates no gaseous organic matters. This publication describes that if the air filter, in which a gaseous organic matter is adsorbed on a filter material thereof through the assembling environment and the packing material, is directly installed in a clean room, the gaseous organic matter is radiated within the clean room and contaminates the air for at least 6-month storage period after the installation. However, although the publication defines a kind of a resin for a resin sheet, and a kind of a plasticizer and an antioxidant as the packing material, no consideration is given regarding influences of other additives, and there is no definition of the amount of an outgas from the packing material. Besides, there is no mention of importance of a packing method of a filter material take-up product. Actually, since the air filter takes a shape where the filter material folded in zigzags is fixed by an aluminum frame or a wooden frame, a surface of the filter material in a packed state is always in contact with or in the vicinity of the packing material, thus susceptible to the exposure of the outgas, which is a harsh condition. On the other hand, when the filter material take-up product for the air filter is packed, the condition for the filter material take-up product is totally different from the above, because only an upper winding of the roll is in contact with the packing material. Therefore, in the publication, no consideration has been given whatsoever to the packed filter material take-up product for the air filter from the standpoint of the outgas.

SUMMARY OF THE INVENTION

However, recent investigation conducted by the inventors has revealed that a source of the outgas generated from the filter material for the air filter is not only a raw material for the filter material but also a packing material of the filter material take-up product, i.e., a coating sheet material or a winding core. That is, most of the outgases generated from the coating sheet material or the winding core of the filter material take-up product stay on an outer portion of a roll or inside of the roll around the winding core. However, a specific outgas permeates into the inside of the filter material take-up product roll to be adsorbed again on the filter material during transport and storage. It was discovered that this filter material on which the specific outgas is adsorbed becomes an outgas source during when the filter material is used. Accordingly, although not all kinds of outgases generated from a packing material need to be controlled, there is now a need to control at least a specific outgas having permeability.

Hence, an object of the present invention is to provide a filter material take-up product for an air filter, which is not contaminated secondarily by an outgas during transport and storage. In other words, the object is to provide a filter material take-up product for an air filter, in which an outgas generated from the filter material take-up product for the air filter is ultimately kept at a negligible level by controlling the amount of the outgas generated from a packing material to as much of a minimum level as possible, for any applications such as building air conditioner, an air cleaner, a semiconductor factory and the like.

Another object of the present invention is to provide a paper-winding core for a filter material take-up product for an air filter, in which an amount of an outgas generated from the paper-winding core is suppressed to as much of a minimum level as possible by defining the amount of the outgas generated from an adhesive used in manufacturing the paper-winding core for taking up the filter material for an air filter. It is also an object to provide a filter material take-up product for an air filter in which this paper-winding core is used.

Yet another object of the present invention is to provide a filter material take-up product for an air filter which is not contaminated secondarily by an outgas even if a storage period of the filter material take-up product for the air filter is long, e.g., 12-month storage period of storage period.

Yet another object of the present invention is to provide a filter material take-up product for an air filter which can be stored for a long period of time without being influenced by an environment of a storage place or an outgas generated from an outer box, by obstructing an influence of a storage environment.

Yet another object of the present invention is to provide a filter material take-up product for an air filter, especially a filter material take-up product for an air filter mainly made of a glass fiber, and also to provide a paper-winding core for the take-up product.

According to the present invention, means for achieving the foregoing objects are as follows.

A filter material take-up product for an air filter according to the present invention is characterized in that a filter material for the air filter wound on a winding core is coated and wrapped with a film wrapping material which has 100 ng/g or less of phenolic compounds, carboxylate esters, phosphate esters and cyclic siloxanes, respectively, as an outgas generation amount when treated by a dynamic head-space method.

A filter material take-up product for an air filter according to the present invention, which includes a filter material for the air filter wound on a winding core, is characterized in that the winding core has 100 ng/g or less of phenolic compounds, carboxylate esters, phosphate esters and cyclic siloxanes, respectively, as an outgas generation amount when treated by a dynamic head-space method.

A paper-winding core for a filter material take-up product for an air filter according to the present invention is characterized in that a winding core on which a filter material is wound is made of paper, and an adhesive used in manufacturing the winding core has 1000 ng/g or less of phenolic compounds, carboxylate esters, phosphate esters and cyclic siloxanes, respectively, as an outgas generation amount when treated by a dynamic head-space method.

A filter material take-up product for an air filter according to the present invention, which includes a filter material for the air filter wound on a winding core, is characterized in that the winding core is made of paper, and an adhesive used in manufacturing the winding core has 1000 ng/g or less phenolic compounds, carboxylate esters, phosphate esters and cyclic siloxanes, respectively, as an outgas generation amount when treated by a dynamic head-space method.

A filter material take-up product for an air filter according to the present invention, which includes a filter material for the air filter wound on a winding core, the filter material being coated and wrapped with a film wrapping material, is characterized in that the winding core and the film wrapping material have 100 ng/g or less of phenolic compounds, carboxylate esters, phosphate esters and cyclic siloxanes, respectively, as a total amount of an outgas when treated by a dynamic head-space method.

A filter material take-up product for an air filter according to the present invention, is characterized in that a filter material for the air filter wound on a winding core is coated and wrapped with a film wrapping material having a gas barrier layer on one side or both sides of a film surface thereof.

A filter material take-up product for an air filter according to the present invention is characterized in that a filter material for the air filter wound on a winding core is coated and wrapped with an aluminum foil sheet.

A filter material take-up product for an air filter according to the present invention, including a filter material for the air filter wound on a winding core, the filter material being coated and wrapped with a film wrapping material, is characterized in that the winding core has 100 ng/g or less of phenolic compounds, carboxylate esters, phosphate esters and cyclic siloxanes, respectively, as an outgas generation amount when treated by a dynamic head-space method, and the film wrapping material is either a film wrapping material having a gas barrier layer on one side or both sides of a film surface thereof, or an aluminum foil sheet.

Concerning the paper-winding core for the filter material take-up product for the air filter of the invention, it is preferable that the filter material for the air filter is mainly made of a glass fiber.

As for the filter material take-up product for the air filter of the invention, preferably, the filter material for the air filter is mainly made of a glass fiber.

In a concept of the film wrapping material of the present invention, a sheet such as an aluminum foil sheet is included.

According to this invention of the filter material take-up product for the air filter, which is not contaminated secondarily by an outgas while being transported or stored, can be provided. This is because the filter material for the air filter, which is wound on the winding core, is coated and wrapped with the film wrapping material in which an outgas generation of phenolic compounds, carboxylate esters, phosphate esters or cyclic siloxanes, respectively by a dynamic head-space method is 100 ng/g or less. This is also because the winding core has an outgas generation of phenolic compounds, carboxylate esters, phosphate esters or cyclic siloxanes, respectively by the dynamic head-space method, is 100 ng/g or less. Accordingly, the filter material for the air filter can be provided in which the amount of the outgas generated therefrom is ultimately kept at a negligible level by controlling the amount of the outgas generated from the packing material to as much of a minimum level as is possible for any applications to a building air conditioner, an air cleaner, a semiconductor factory or the like.

According to this invention, by defining the amount of outgas generated from the adhesive used in manufacturing a paper-winding core for a filter material for the air filter, the paper-winding core for a filter material take-up product for the air filter, where an amount of an outgas generated from the paper-winding core is suppressed to as much of an minimum level as is possible, as well as a filter material take-up product for the air filter using the paper-winding core can be provided.

According to this invention a winding core and a film wrapping material are used, and the winding core and the film wrapping material have 100 ng/g or less of phenolic compounds, carboxylate esters, phosphate esters and cyclic siloxanes, respectively as a total amount of an outgas generation amount when treated by a dynamic head-space method. Thus, a filter material take-up product for the air filter, which is not contaminated secondarily by the outgas even though being stored for a long period of time, e.g., 12-month storage period, can be provided.

According to this invention, an influence of a storage environment is obstructed by coating and wrapping the filter material take-up product for the air filter, with a film wrapping material having a gas barrier layer on one side or both sides of the film surface thereof or with an aluminum foil sheet, or by using either of the film wrapping material or the aluminum foil sheet together with a winding core which has 100 ng/ng or less of phenolic compounds, carboxylate esters, phosphate esters and cyclic siloxanes, respectively, as an outgas generation amount when treated by the dynamic head-space method. Therefore, the filter material take-up product for the air filter, which can be stored for a long period of time without being influenced by the environment of a storage place or the outgas generated from the outer box, can be provided.

According to this invention, the filter material for the air filter, especially the filter material take-up product for the air filter mainly made of glass fiber, and the paper-winding core for the take-up product can be provided.

DETAILED DESCRIPTION OF THE INVENTION

Next, the present invention is described in detail, but it should be appreciated that the invention is not limited to embodiments described below.

With regard to a film wrapping material or a winding core of the present invention, a minimum amount of a substance containing phenolic compounds represented by 2, 6-di-t-butyl-p-cresol (BHT) used for an antioxidant or the like, carboxylate esters such as a phthalate ester represented by DOP, DBP used for a plasticizer or the like or a maleate ester, phosphate esters represented by triethyl phosphate (TEP) used for a fire retardant or the like, tributyl phosphate (TBP) or cyclic siloxanes contained in silicone oil used for a plastic mold-releasing agent or the like is used. The generation amount of an outgas (referred to as a specific outgas, hereinafter), which is each of the above-described substances, is set to 100 ng/g or less.

Here, the generation amount of an outgas means a numerical value per sample 1 g, which is obtained in the following manner: A sample is heated in an inert gas flow at 80° C. for 1 hour, an outgas generated from the sample is gathered and condensed using an absorbent, and then the outgas is measured by a gas chromatograph mass spectrometer. Then the numerical value is calculated from a peak area obtained by the gas chromatograph mass spectrometer as n-hexadecane by the use of an n-hexadecane calibration curve.

As a result of dedicated investigations by the inventors, it was discovered that the specific outgas is easily stacked especially to a glass fiber surface and, when a take-up product is wrapped, the specific outgas has characteristics to permeate into the inside of a roll and adsorbed. As the specific outgas, there are phenolic compounds, carboxylate esters and phosphate esters which respectively have a molecular weight of 150 or higher having a relatively high boiling point, and cyclic siloxanes with silicon numbers of 10 or less which, in particular, tends to be adsorbed easily.

Normally, it is considered difficult for the outgas to permeate into the inside of a roll because it is blocked by the surface of the winding roll. However, unlike a generally-used sheet for printing and wrapping, the glass fiber filter material has a porosity of about 90 to 95% and an average pore diameter of 2 to 100 μm, which are considerably large. Thus, an outgas of an angstrom order may permeate relatively easily without being prevented by a roll surface or a roll end. Additionally, the glass fiber surface is in a state where a chemical adsorption easily occurs because of the presence of an oxygen atom which is slightly charged negatively, and an alkaline metal such as sodium, potassium, calcium, magnesium etc., or alkaline rare earth metal atom which is slightly charged positively.

On the other hand, an outgas of hydrocarbon or a substance other than the above-described substances has characteristics that the permeation into the inside of the roll as well as adsorption are less likely to occur, although the outgas is absorbed on the portion with which the outgas is in direct contact or on the vicinity of the portion. This may be attributed to the fact that these outgases have lower characteristics in respect of absorption to the glass fiber surface compared with those of the specific outgas.

Accordingly, it has been newly discovered that the object of the present invention can be achieved by paying attention to the specific outgas having high adsorption characteristics to the glass fiber, and by controlling the amount of the specific outgas. The specific outgas is phenolic compounds, carboxylate esters, phosphate esters, or cyclic siloxanes, and was selected based on the knowledge gained through the painstaking investigations by the inventors.

Further, it has been discovered that, in a filter material for an air filter whose raw material is a fiber other than a glass fiber, i.e., an organic compound fiber nonwoven filter material, an electret nonwoven filter material and a PTFE film filter material, the specific outgas exhibits a behavior similar to that in a filter material take-up product made of a glass fiber. This may be attributed to the fact that the porosity and the average pore diameter of a filter material for an air filter are generally large similarly to the filter material made of a glass fiber, and therefore the outgas permeates easily, and adsorption characteristics onto the fiber surface is high in respect of the specific outgas. For example, the electret nonwoven filter material has a structure where a surface of polypropylene fiber is polarized to be charged positively and negatively, and thus may be in the state where a chemical adsorption easily occurs. The PTFE film filter material has a fiber of which the diameter is even smaller than that of the glass fiber due to extension of the film. It is thus speculated that the PTFE film filter material has a large specific surface area and is in the condition where a physical adsorption easily occurs.

Regarding the packed take-up product stored for a 12-month storage period, a ratio of a packing material (a film wrapping material and winding core) and the take-up product as the outgas sources was investigated. This investigation revealed that the ratio ranged from approximately {fraction (1/100)} to {fraction (1/1000)} of the filter material and the packing material, respectively, as the sources of each specific outgases. That is, if the amount of each specific outgas generated from the packing material is controlled to be 100 ng/g or less, the amount of outgas, generated from the packing material, of each component adsorbed again on the take-up product can be controlled to an order of 1 to 0.1 ng/g or less. If this order is maintained, there are no practical problems.

A quantitative detection limit of outgas amount measurement of the present invention is 1 ng/g. It is highly likely that the limit of 1 ng/g may cause a problem in a clean room. Additionally, since the longest storage period of the take-up product is one year, this limit of the outgas amount is a maximum value. Thus, in a product stored for a shorter period than 1 year, an amount of an outgas adsorbed again on the filter material for the air filter generated from the packing material or the like may be smaller.

A film wrapping material used in the present invention is a film material whose raw material is polyethylene, polypropylene, polyester, nylon, polyvinyl chloride, polyvinylidene chloride or the like. As the film wrapping material, a film material is selected among those having 100 ng/g or less of phenolic compounds, carboxylate esters, phosphate esters or cyclic siloxanes, respectively, as an outgas generation amount when treated by a dynamic head-space method.

As a type of the wrapping material, there are a sheet type, a bag type formed in a cylindrical shape, one side of its open part being closed by a method such as heat sealing, etc. The type is not specifically limited as long as there is no problem regarding packing works or the type itself. A thickness of the film is set in a range of 10 to 100 μm. As far as the size is concerned, the packing material need to be large enough to coat and wrap the take-up product which has a widely-ranged diameter from about 30 to 100 cm and a width of about 20 to 150 cm.

The winding core of the invention is a core in a cylindrical shape. The filter material for the air filter that is continuously manufactured by a paper machine is, in the last part of the process, wound first on the cylindrical core in a taking-up process after the filter material is slit into a set width.

A raw material of the winding core is selected from a resin, paper and a metal. As for the resin, various raw materials can be used, such as an ABS resin, a PP resin, a polyester resin, and an epoxy resin. It is also possible to use a resin reinforced by a glass fiber or a carbon fiber. In any case, it is necessary to use the winding core which has 100 ng/g or less of phenolic compounds, carboxylate esters, phosphate esters and cyclic siloxanes, respectively, as an outgas generation amount when treated by the dynamic head-space method. As the paper-winding core, there is a so-called "paper tube" in which used paper or kraft paper is cylindrically wound while applying an adhesive thereon. As the metal winding core, iron or aluminum is used. However, such a metal winding core is difficult be used because it is generally high in weight and price. The cylindrical core has a thickness of 1 mm to several tens of mm, a diameter and a width which are varied, and a core which meets product take-up conditions and product dimensions is selected as a winding core.

Since a component of the specific outgas is often contained in a sub-raw material of a resin or the paper adhesive, the winding core made of a resin or paper, in particular, is to be selected from those having 100 ng/g or less of phenolic compounds, carboxylate esters, phosphate esters or cyclic siloxanes, respectively, as an outgas generation amount when treated by the dynamic head-space method.

The adhesive for the paper-winding core, in particular, should be selected from those having 1000 ng/g or less of the generation amount of phenolic compounds, carboxylate esters, phosphate esters and cyclic siloxanes, respectively, of the specific outgas of the specific outgas component per adhesive solid part, when treated by the dynamic head-space method. This is for controlling the outgas generation amount of phenolic compounds, carboxylate esters, phosphate esters and cyclic siloxanes, respectively, from the winding core to be 100 ng/g or less, since the paper-winding core generally contains an adhesive amount of 10 % or less: The use of the paper-winding core facilitates disposal.

For a packing method, it is effective to use either a film wrapping material, which has 100 ng/g or less of phenolic compounds, carboxylate esters, phosphate esters and cyclic siloxanes, respectively, as an outgas generation amount when treated by the dynamic head-space method, or a winding core, which has 100 ng/g or less of phenolic compounds, carboxylate esters, phosphate esters and cyclic siloxanes, respectively, as an outgas generation when treated by the dynamic head-space method. However, it is more preferable if both of the film wrapping material and the winding core have 100 ng/g or less of phenolic compounds, carboxylate esters, phosphate esters and cyclic siloxanes, respectively, as the total amount of the outgas generation amount when treated by the dynamic head-space method. This is because the wrapping material does not give any problematic influences on the take-up product even if the product is stored up to 1 year. In the case where only the film wrapping material or the winding core has 100 ng/g or less of phenolic compounds, carboxylate esters, phosphate esters and cyclic siloxanes, respectively, as an outgas generation when treated by the dynamic head-space method, a countermeasure such as to shorten the storage period needs to be taken.

As described earlier, the take-up product wrapped by the film is housed in an outer box made of a cardboard or other material for the purpose of maintaining the strength of the product during transport or piling up stocks for storage. The outgas generated from such a material is blocked to a certain extent by the film wrapping material, and therefore adsorption on the product can be prevented. However, since there are no complete gas-blocking effects, use of an outer box containing a small amount of a specific outgas component is desirable, although the influence by the outer box is not as large as that by the film wrapping material or the winding core.

Additionally, as another generation source of the specific outgases, there is an influence by an environment of a storage place for transport or storage. As a countermeasure to this influence, or as the aforementioned measure to an outer box influence, wrapping of the product roll by a gas-barrier wrapping material is a more preferable packing method. Further, it is more preferable that the filter material for the air filter or a take-up product thereof is first coated and wrapped by a film wrapping material which has 100 ng/g or less of phenolic compounds, carboxylate esters, phosphate esters and cyclic siloxanes, respectively, as an outgas generation amount when treated by the dynamic head-space method, and then coated and wrapped by a wrapping material having the gas-barrier characteristics.

As the gas-barrier wrapping material, an aluminum foil sheet or a film, in which aluminum, silica or alumina is vacuum deposited on at least one side of the film, is used. For the aluminum foil sheet, a sheet having a thickness of about 10 to 50 µm is used, and a sheet where paper, a plastic film, moisture-proof cellophane, wax glassine paper or the like is bonded on one side thereof can also be used. As the vacuum-deposited film, a film is used which is formed by depositing aluminum, silica or alumina to about 50 nm to 10 µm on a film base thereof made of polyester, PP, polyethylene, nylon, polyvinyl chloride, polyvinylidene chloride or the like. As the film base, it is preferable to use a base, which has 100 ng/g or less of phenolic compounds, carboxylate esters, phosphate esters and cyclic siloxanes, respectively, as an outgas generation amount when treated by the dynamic head-space method. However, the base is not limited to this since, if the deposited side of the vacuum-deposited film is faced to the product roll in wrapping, the outgas generated from the film can be blocked. The same can be said for the one-side bonding of an aluminum foil sheet. Note that the aluminum foil sheet is easily torn, and has a certain rigidity, thereby the filter material product may be damaged. Thus, adequate care is necessary in handling the product during wrapping work. In this regard, the vacuum-deposition film is handled relatively easily. As for both of the aluminum foil sheet and the vacuum-deposited film, those having a minimum number of or no pinholes are preferable. There is no way of preventing the outgas emanating from a winding core. Therefore, as a winding core used together with either one of the films above, it is more preferable to use the one having 100 ng/g or less of phenolic compounds, carboxylate esters, phosphate esters and cyclic siloxanes, respectively, as an outgas generation amount when treated by the dynamic head-space method.

Here, as the measuring method of the outgas of the present invention, so-called dynamic head-space method was used. First, by using a condensation/injection apparatus for the generated gas (by GL Sciences Inc. MSTD-258), a sample of about 0.2 g was heated in an inert He gas flow (flow rate of 50 ml/min.) with a purity of 99.999% at 80° C. for 1 hour. An outgas generated from the sample was gathered and condensed by an adsorbent (TENAX TA). Then, after a sample band was narrowed by a cryofocus unit, the gas desorbed again at 270° C. was injected to a gas chromatograph mass spectrometer (by Shimazu Corporation, GCMS-QP5050A) and measured. For a capillary column, TC-1 (by GL Sciences Inc., 0.25 mm×60 m, film pressure 0.25 µm) was used. An ionizing method of the mass spectrometer was an electron impact method (ionizing voltage of 70 eV). Since the generated outgas component is easily adsorbed to a test chamber for housing and heating the sample, a pipe, and other members, a measurement result could be affected, and therefore a consideration need to be given to the material thereof or the like. Here, a test chamber made of quartz glass, and a stainless-made flow path pipe with a quartz-coated inner surface were used, and further heated at 270° C. to prevent adsorption of a very small amount of a gas such examples and comparative examples.

EXAMPLES

Next, the present invention is explained more specifically referring to examples and comparative examples. However, it should be appreciated that the present invention is not limited to them.

Example 1

A filter material take-up product for HEPA (width of 610 mm, winding length of 1000 m) wound on a kraft paper-winding core commercial product A (diameter of 108 mm, thickness of 17 mm, width of 610 mm) in which a DBP outgas amount is 53 ng/g was wrapped by a polyethylene film bag commercial product a (thickness of 30 μm) in which a BHT outgas amount is 14 ng/g, and then housed in a cardboard box and packed. After 3-month storage period of storage in a warehouse, the take-up product was torn, sampling was carried out from a center of the roll (to an approximate winding length of 500 m), and outgas measurement of the filter material was carried out. Note that, from the HEPA filter material before packing, no specific outgas was detected.

Example 2

Outgas measurement of a filter material was carried out similarly to the example 1, except that a take-up product after packing was stored for a period of 12-month storage period.

Example 3

Outgas measurement of a filter material was carried out similarly to the example 1, except that a polyethylene film bag commercial product b (thickness of 50 μm) in which a BHT outgas amount is 252 ng/g was used as a film wrapping material.

Example 4

A small amount of the HEPA filter material of the example 1 was sampled before packing, and cut into an A4 size. Then 100 sheets of the material was stacked and wrapped by an aluminum foil sheet commercial product a (thickness of 12 μm) having a non-glossy side of the sheet facing inside. In this case, in order to prevent gas from entering, the end of the sheet was folded inwardly such that both the non-glossy sides meet, and fixed by a cellophane tape to be tightly sealed. This wrapped material was further wrapped by a film wrapping material which is a polyethylene film bag commercial product c (thickness of 30 μm) in which a BHT outgas amount is 114 ng/g, in order to create a contrived environment where a an exposure to the BHT gas can take place. After leaving the material for 3-month storage period in a room, sampling was carried out from a center of the material middle layer of the 100-stacked filter material sheets, and outgas measurement of the filter material was carried out.

Comparative Example 1

A filter material take-up product for HEPA (width of 610 mm, winding length of 1000 m) wound on a kraft paper-winding core commercial product B (diameter of 108 mm, thickness of 17 mm, width of 610 mm), in which a DBP outgas amount is 3800 ng/g, and a BHT outgas amount is 387 ng/g, was wrapped by a polyethylene film bag commercial product c (thickness of 30 μm) in which a BHT outgas amount is 1140 ng/g, and then housed in a cardboard box and packed. After 12-month storage period of storage in a warehouse, a filter material roll was torn, sampling was carried out from a center part of a middle layer of the roll (to at an approximate winding length of 500 m), and outgas measurement of the filter material was carried out.

Comparative Example 2

Outgas measurement of a filter material was carried out similarly to the comparative example 1, except that the storage period in a warehouse was 3-month storage period.

Comparative Example 3

Outgas measurement of a filter material was carried out similarly to the comparative example 2, except that the film wrapping material of the example 3 was used.

Comparative Example 4

Outgas measurement of a filter material was carried out similarly to the example 4 except for the use of the film wrapping material of the example 1, i.e., the commercial product a, in place of the aluminum foil sheet.

Outgas measurement results of the examples 1 to 3 and the comparative examples 1 to 3 are as shown in Table 1.

TABLE 1

|  |  | Example 1 | Example 2 | Reference 1 | Comparative Example 1 | Comparative Example 2 | Comparative Example 3 |
|---|---|---|---|---|---|---|---|
| Film wrapping material | | Commercial product a | Commercial product a | Commercial product b | Commercial product c | Commercial product c | Commercial product b |
| Winding core | | Commercial product A | Commercial product A | Commercial product A | Commercial product B | Commercial product B | Commercial product B |
| Product roll storage period | | 3 months | 12 months | 3 months | 12 months | 3 months | 3 months |
| Film wrapping material | Phenolic compound | BHT 14 ng/g | BHT 14 ng/g | BHT 252 ng/g | BHT 1140 ng/g | BHT 1140 ng/g | BHT 252 ng/g |
| | Carboxylate ester | Quantitative detection limit or lower | Quantitative detection limit or lower | Quantitative detection limit or lower | Quantitative detection limit or lower | Quantitative detection limit or lower | Quantitative detection limit or lower |
| | Phosphate ester | Quantitative detection limit or lower | Quantitative detection limit or lower | Quantitative detection limit or lower | Quantitative detection limit or lower | Quantitative detection limit or lower | Quantitative detection limit or lower |
| | Cyclic siloxane | Quantitative detection limit or lower | Quantitative detection limit or lower | Quantitative detection limit or lower | Quantitative detection limit or lower | Quantitative detection limit or lower | Quantitative detection limit or lower |

TABLE 1-continued

| | | Example 1 | Example 2 | Reference 1 | Comparative Example 1 | Comparative Example 2 | Comparative Example 3 |
|---|---|---|---|---|---|---|---|
| Winding core | Phenolic compound | Quantitative detection limit or lower | Quantitative detection limit or lower | Quantitative detection limit or lower | BHT 387 ng/g | BHT 387 ng/g | BHT 387 ng/g |
| | Carboxylate ester | DBP 53 ng/g | DBP 53 ng/g | DBP 53 ng/g | DBP 3800 ng/g | DBP 3800 ng/g | DBP 3800 ng/g |
| | Phosphate ester | Quantitative detection limit or lower | Quantitative detection limit or lower | Quantitative detection limit or lower | Quantitative detection limit or lower | Quantitative detection limit or lower | Quantitative detection limit or lower |
| | Cyclic siloxane | Quantitative detection limit or lower | Quantitative detection limit or lower | Quantitative detection limit or lower | Quantitative detection limit or lower | Quantitative detection limit or lower | Quantitative detection limit or lower |
| HEPA filter material (after storage) | Phenolic compound | Quantitative detection limit or lower | Quantitative detection limit or lower | Quantitative detection limit or lower | BHT 15 ng/g | BHT 3.7 ng/g | BHT 1.6 ng/g |
| | Carboxylate ester | Quantitative detection limit or lower | Quantitative detection limit or lower | Quantitative detection limit or lower | DBP 34 ng/g | DBP 7.3 ng/g | DBP 8.5 ng/g |
| | Phosphate ester | Quantitative detection limit or lower | Quantitative detection limit or lower | Quantitative detection limit or lower | Quantitative detection limit or lower | Quantitative detection limit or lower | Quantitative detection limit or lower |
| | | Quantitative detection limit or lower | Quantitative detection limit or lower | Quantitative detection limit or lower | Quantitative detection limit or lower | Quantitative detection limit or lower | Quantitative detection limit or lower |

In the example 1, the packing method using the film wrapping material and the winding core, both of which have a specific outgas amount of 100 ng/g or less was employed with a 3-month storage period, and all of the specific outgases generated from the filter material were equal to or lower than a quantitative detection limit. Further, in the example 2, where the same packing method was employed with the storage period of up to 12-month storage period, specific outgases were also equal to or lower than a quantitative detection limit.

In Reference 1, where the generation amount of specific outgases, respectively was 100 ng/g or less in respect of the winding core only, specific outgases generated from the filter material after stored for 3-month storage period were all equal to or lower than a quantitative detection limit. This is an example which shows that it is not a problem even if either one of the film wrapping material or the winding core does not satisfy the generation amount of specific outgases, respectively of 100 ng/g or less, as long as a storage period is short.

On the other hand, in the comparative examples 1 and 2 where certain specific outgas amounts were 100 ng/g or more in respect of both of the film wrapping material and the winding core, not only after 12-month storage period of storage but also after 3-month storage period of storage, specific outgases (BHT, DBP) were detected from the filter material.

In the comparative example 3, even though the film wrapping material of the example 3 was used, not only DBP but also BHT were detected. This is considered to be attributed to the addition of a BHT gas generated from the winding core.

Outgas measurement results of the example 4 and the comparative example 4 are as shown in Table 2.

TABLE 2

| | | Example 4 | Comparative example 4 |
|---|---|---|---|
| Storage period | | 3 months | 3 months |
| Wrapping material | | Aluminum foil sheet commercial product α | Polyethylene film commercial product a |
| HEPA filter material | Phenolic compound | quantitative detection limit or lower | BHT 1.2 ng/g |
| | Carboxylate | quantitative detection | quantitative detection |

TABLE 2-continued

| | | Example 4 | Comparative example 4 |
|---|---|---|---|
| (after storage) | ester | limit or lower | limit or lower |
| | Phosphate ester | quantitative detection limit or lower | quantitative detection limit or lower |
| | Cyclic siloxane | quantitative detection limit or lower | quantitative detection limit or lower |

In the example 4, where the wrapping with the aluminum foil sheet having gas-barrier characteristics was employed, the BHT gas generated from the film material was blocked, and therefore no specific outgases were detected from the filter material. On the other hand, in the comparative example 4, the gas-barrier characteristics of the film wrapping material was lower than that of the aluminum foil sheet. It is thus considered that the BHT gas, which permeated through the film and was adsorbed on the filter material, was detected.

Example 5

For a replacement filter (CAF-45H1FS) of an air cleaner by Toshiba Inc., an electret nonwoven filter material (coulomb HEPA filter) was taken out after removing an outer frame and an active carbon filter, and cut into a size of 15×15 cm. This filter material was placed in a container under suction, and baking process was carried out to humidify the container in a hot bath at 90° C. for 3 days. Then, 100 filter material sheets after the baking were stacked, and laid on the kraft paper-winding core A of the example 1 that has been cut into half in a longitudinal direction. These material sheets were wrapped by the polyethylene film bag commercial product a of the example 1 in order to create a similar state to that of the take-up product after packing. After 3-month storage period storage in a room, sampling was carried out from a center of a middle layer of the 100 stacked filter material sheets, and outgas measurement of the filter materials was carried out. Note that no specific outgases were detected from the filter materials after the baking.

Example 6

A PTFE film filter material (PTFE type membrane filter T100A142C; dimension of 142 φmm) by Advantec Toyo, Ltd. was subjected to a baking process similar to that in the example 5. Then, 100 sheets of the filter material after baking were stacked, and processed similarly to the example 5, and then outgas measurement of the filter material was carried out. Note that any of this specific outgases were not detected from the filter material after the backing.

Comparative Example 5

Outgas measurement of a filter material was carried out similarly to the example 5 except for the use of the winding core and the film wrapping material of the comparative example 1, i.e., the kraft paper-winding core commercial product B and the polyethylene film bag commercial product c, respectively.

Comparative Example 6

Outgas measurement of a filter material was carried out similarly to the example 6 except for the use of the winding core and the film wrapping material of the comparative example 1, i.e., the kraft paper-winding core commercial product B and the polyethylene film bag commercial product c, respectively.

Results are shown in Table 3.

In the example 5, a packing method using the film wrapping material and the winding core, which respectively have a specific outgas amount of 100 ng/g or less, was employed with a 3-month storage period. All of the specific outgases generated from the electret nonwoven filter material were equal to or lower than a quantitative detection limit.

Similarly, in the example 6, a packing method using the film wrapping material and the winding core, which respectively have a specific outgas amount of 100 ng/g or less was employed with a 3-month storage period. All specific outgases generated from the PTFE film filter material were equal to or lower than a quantitative detection limit.

On the other hand, in the comparative examples 5 and 6, where the amount of a certain specific outgas was 100 ng/g or more in respect of both of the film wrapping material and the winding core, the specific outgases (BHT, DBP) were detected from the filter material.

From the results of the examples 5 and 6, it was understood that not only for the filter material for the air filter mainly made of a glass fiber but also for the electret nonwoven filter material and the PTFE film filter material, to control the amount of the specific outgas generation from the film wrapping material and the winding core is effective for suppressing outgas generation from the filter material for the air filter after the storage.

The filter material take-up product for the air filter of the present invention can be used for a clean room, a clean bench

TABLE 3

| | | Example 5 | Example 6 | Comparative example 5 | Comparative example 6 |
|---|---|---|---|---|---|
| | Filter material | Electret Nonwoven Filter material | PTFE film filter material | Electret Nonwoven Filter material | PTFE film filter material |
| | Film wrapping material | Commercial product a | Commercial product a | Commercial product c | Commercial product c |
| | Winding core | Commercial product A | Commercial product A | Commercial product B | Commercial product B |
| | Storage period | 3 months | 3 months | 3 months | 3 months |
| Film wrapping material | Phenolic compound | BHT 14 ng/g | BHT 14 ng/g | BHT 1140 ng/g | BHT 1140 ng/g |
| | Carboxylate ester | quantitative detection limit or lower | quantitative detection limit or lower | quantitative detection limit or lower | quantitative detection limit or lower |
| | Phosphate ester | quantitative detection limit or lower | quantitative detection limit or lower | quantitative detection limit or lower | quantitative detection limit or lower |
| | Cyclic siloxane | quantitative detection limit or lower | quantitative detection limit or lower | quantitative detection limit or lower | quantitative detection limit or lower |
| Winding core | Phenolic compound | quantitative detection limit or lower | quantitative detection limit or lower | BHT 387 ng/g | BHT 387 ng/g |
| | Carboxylate ester | DBP 53 ng/g | DBP 53 ng/g | DBP 3800 ng/g | DBP 3800 ng/g |
| | Phosphate ester | quantitative detection limit or lower | quantitative detection limit or lower | quantitative detection limit or lower | quantitative detection limit or lower |
| | Cyclic siloxane | quantitative detection limit or lower | quantitative detection limit or lower | quantitative detection limit or lower | quantitative detection limit or lower |
| HEPA filter material (after storage) | Phenolic compound | quantitative detection limit or lower | quantitative detection limit or lower | BHT 2.3 ng/g | BHT 1.1 ng/g |
| | Carboxylate ester | quantitative detection limit or lower | quantitative detection limit or lower | DBP 3.5 ng/g | DBP 1.8 ng/g |
| | Phosphate ester | quantitative detection limit or lower | quantitative detection limit or lower | quantitative detection limit or lower | quantitative detection limit or lower |
| | Cyclic siloxane | quantitative detection limit or lower | quantitative detection limit or lower | quantitative detection limit or lower | quantitative detection limit or lower | or the like for a semiconductor, a liquid crystal or a bio/food industry, or an air filter for a building air conditioner, an air cleaner etc.

What is claimed is:

1. A filter material take-up product for an air filter, comprising a filter material which is wound on a winding core, the winding core and a plastic film wrapping material, characterized in that at least one of said winding core and the plastic film wrapping material have an outgas generation amount, when treated by a dynamic head-space method, of 100 ng/g or less of phenolic compounds, carboxylate esters, phosphate esters, having a molecular weight of 150 or more, and cyclic siloxanes having 10 or less silicon atoms, respectively, and also, outgas generating amount is not regulated except aforesaid outgas.

2. The product of claim 1, wherein the winding core is made of paper, and an adhesive used in manufacturing the winding core has an outgas generation amount, when treated by a dynamic head space method, of 1000 ng/g or less of phenolic compounds, carboxylate esters, phosphate esters each having a molecular weight of 150 or more, and cyclic siloxanes having 10 or less silicon atoms, respectively, and also, outgas generating amount is not regulated except aforesaid outgas.

3. The filter material take-up product for an air filter according to claim 1 or 2 wherein the filter material which is wound on the winding core for the air filter is mainly made of a glass fiber.

* * * * *